(12) United States Patent
Wong et al.

(10) Patent No.: US 10,690,595 B2
(45) Date of Patent: Jun. 23, 2020

(54) OPTICAL SENSING DEVICE, METHOD OF MANUFACTURING THE SAME, AND OPTICAL SENSING METHOD

(71) Applicant: Agency for Science, Technology and Research, Singapore (SG)

(72) Inventors: Chi Lok Wong, Singapore (SG); Malini Olivo, Singapore (SG)

(73) Assignee: Agency for Science, Technology and Research, Singapore (SG)

(*) Notice: Subject to any disclaimer, the term of this patent is extended or adjusted under 35 U.S.C. 154(b) by 0 days.

(21) Appl. No.: 16/319,155

(22) PCT Filed: Jul. 18, 2017

(86) PCT No.: PCT/SG2017/050355
§ 371 (c)(1),
(2) Date: Jan. 18, 2019

(87) PCT Pub. No.: WO2018/017017
PCT Pub. Date: Jan. 25, 2018

(65) Prior Publication Data
US 2019/0285542 A1    Sep. 19, 2019

(30) Foreign Application Priority Data
Jul. 20, 2016   (SG) .............................. 10201605957P

(51) Int. Cl.
*G01J 4/00*    (2006.01)
*G01N 21/552*  (2014.01)
(Continued)

(52) U.S. Cl.
CPC .......... *G01N 21/553* (2013.01); *G01J 3/0224* (2013.01); *G01J 3/447* (2013.01);
(Continued)

(58) Field of Classification Search
CPC ................. G01N 21/211; G01N 21/21; G01N 2021/213; G01J 4/00; G01B 11/0641
(Continued)

(56) References Cited

U.S. PATENT DOCUMENTS

2008/0158549 A1   7/2008  Lee et al.
2014/0016098 A1*  1/2014  Matsumoto .......... G03B 21/204
                                                  353/20

FOREIGN PATENT DOCUMENTS

CN    102042972 A    5/2011
JP    2001-041881 A  2/2001

OTHER PUBLICATIONS

Written Opinion of the International Searching Authority for International Application No. PCT/SG2017/050355 dated Oct. 19, 2017, pp. 1-5.
(Continued)

*Primary Examiner* — Md M Rahman
(74) *Attorney, Agent, or Firm* — Winstead PC

(57) ABSTRACT

Various embodiments may provide an optical sensing device based on surface plasmon resonance (SPR). The optical sensing device may include an optical arrangement configured to provide a first polarization light beam and a second polarization light beam, and a first optical member including a sensing surface, the first optical member configured to receive the first and second polarization light beams and reflect the first and second polarization light beams at the sensing surface. The optical sensing device may further include a second optical member arranged to receive the reflected first and second polarization light beams from the first optical member and configured to separate the reflected first and second polarization light beams in a first direction and a second direction, respectively. The optical device may additionally include a detector arrangement configured to
(Continued)

detect the reflected first and second polarization light beams from the second optical member.

10 Claims, 10 Drawing Sheets

(51) Int. Cl.
    *G01N 21/21*      (2006.01)
    *G01J 3/447*      (2006.01)
    *G01N 33/543*      (2006.01)
    *G01J 3/02*      (2006.01)
    *G01N 21/05*      (2006.01)
    *G01N 21/77*      (2006.01)

(52) U.S. Cl.
    CPC ............... *G01J 4/00* (2013.01); *G01N 21/21* (2013.01); *G01N 33/54373* (2013.01); *G01N 21/05* (2013.01); *G01N 2021/212* (2013.01); *G01N 2021/7753* (2013.01)

(58) Field of Classification Search
    USPC ........................................................ 356/369
    See application file for complete search history.

(56) References Cited

OTHER PUBLICATIONS

International Preliminary Report on Patentability for International Application No. PCT/SG2017/050355 dated Mar. 22, 2018, pp. 1-23.

\* cited by examiner

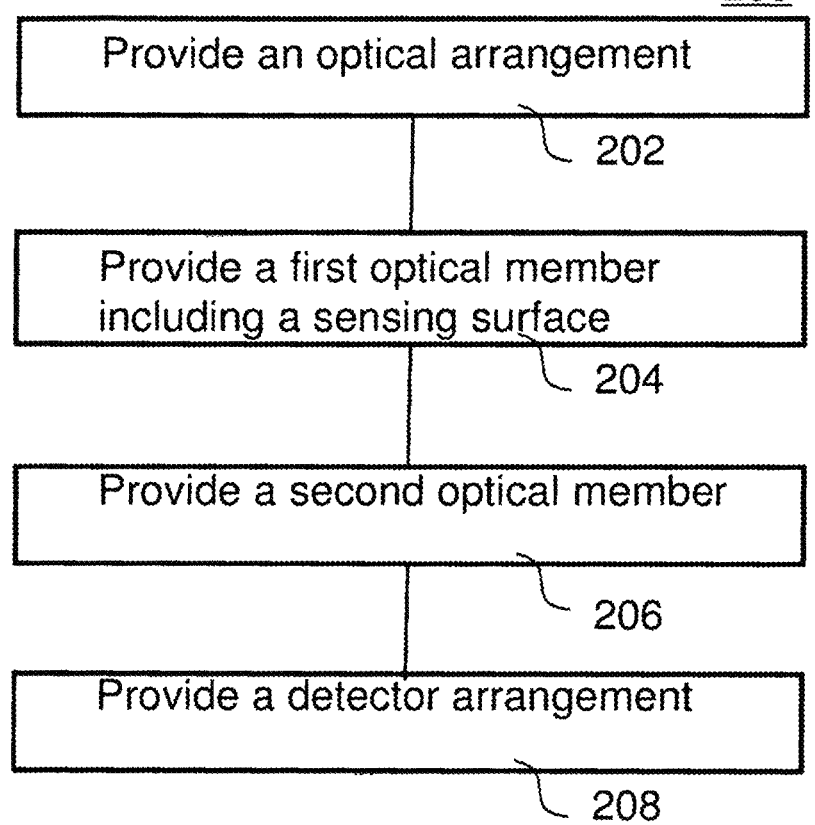

FIG. 3  300

- Provide a sample on a first optical member — 302
- Provide a first polarization light beam and a second polarization light beam — 304
- Reflect the first and second polarization light beams at the sensing surface — 306
- Separate the reflecting first and second polarization light beams received from the first optical member in a first direction and a second direction — 308
- Detect the reflected first and second polarization light beams from the second optical member — 310

OPTICAL SENSING DEVICE, METHOD OF MANUFACTURING THE SAME, AND OPTICAL SENSING METHOD

CROSS-REFERENCE TO RELATED APPLICATION

This application claims the benefit of priority of Singapore application No. 10201605957P filed on Jul. 20, 2016, the contents of it being hereby incorporated by reference in its entirety for all purposes.

TECHNICAL FIELD

Various aspects of this disclosure relate to optical sensing devices and/or methods of manufacturing the same. Various aspects of this disclosure relate to optical sensing methods.

BACKGROUND

In recent times, protein biomarkers have been gaining rapid research interests. Early disease diagnosis and treatment response assessment are made possible with the detection of protein biomarker expression levels in patient samples. Protein biomarkers for cancers, heart diseases and infectious diseases have been reported to date. Characterization of the activity and binding kinetics of the protein biomarkers allow for structural analysis, development of screening assays and lead optimization.

The most commonly used detection methods for biomarker discovery are mass spectroscopy, two-dimensional (2D) western blotting, 2D gel electrophoresis, and enzyme-linked immunosorbent assay (ELISA). In addition, microarray technology has recently also become an effective alternative for biomarker profiling. Common strategies for antibody microarray detection includes direct target labeling, sandwich assay, and competitive adsorption assay, in which fluorescent labeling, secondary antibodies or enzyme are required in the detection process. Different fluorescently labeled molecules or secondary antibodies are required for each array elements in the antibody array detection. Although mass spectroscopy, 2D western blotting, 2D gel electrophoresis and ELISA detection methods identify whether interactions are present between protein and other molecules, they do not give further information on the binding kinetics of the interactions, which is important to determine drug efficacy. Furthermore, these methods require long detection and preparation processes.

Surface plasmon resonance (SPR) is a sensitive label-free alternative for the detection of biomolecular interactions such as protein-protein interactions. SPR measures the refractive index changes associated with the protein-protein binding occurring at the gold sensing surface. In addition to providing real-time responses for rapid detection, SPR also provides information on protein-protein binding equilibrium and kinetics. Common intensity-based SPR sensors rely on the intensity change produced by the shift of SPR absorption minimum wavelength at resonance. However, such sensors can only provide limited sensor resolution at $10^{-5}$ refractive index units (RIUs).

SUMMARY

Various embodiments may provide an optical sensing device based on surface plasmon resonance (SPR). The optical sensing device may include an optical arrangement configured to provide a first polarization light beam and a second polarization light beam. The optical sensing device may also include a first optical member including a sensing surface, the first optical member configured to receive the first and second polarization light beams and reflect the first and second polarization light beams at the sensing surface. The optical sensing device may further include a second optical member arranged to receive the reflected first and second polarization light beams from the first optical member and configured to separate the reflected first and second polarization light beams in a first direction and a second direction, respectively. The optical device may additionally include a detector arrangement configured to detect the reflected first and second polarization light beams from the second optical member.

Various embodiments may provide a method of manufacturing an optical sensing device based on surface plasmon resonance (SPR). The method may include providing an optical arrangement configured to provide a first polarization light beam and a second polarization light beam. The method may also include providing a first optical member including a sensing surface, the first optical member configured to receive the first and second polarization light beams and reflect the first and second polarization light beams at the sensing surface. The method may further include providing a second optical member arranged to receive the reflected first and second polarization light beams from the first optical member and configured to separate the reflected first and second polarization light beam in a first direction and a second direction, respectively. The method may also include providing a detector arrangement configured to detect the reflected first and second polarization light beams from the second optical member.

Various embodiments may provide an optical sensing method based on surface plasmon resonance (SPR). The method may include providing a sample on a first optical member, the first optical member including a sensing surface on which the sample is provided. The method may also include providing, by an optical arrangement, a first polarization light beam and a second polarization light beam to the first optical member. The method may further include reflecting the first and second polarization light beams at the sensing surface to provide a reflected first polarization light beam and a reflected second polarization light beam. The method may additionally include separating, by a second optical member, the reflecting first and second polarization light beams received from the first optical member in a first direction and a second direction, respectively. The method may also include detecting, by a detector arrangement, the reflected first and second polarization light beams from the second optical member.

BRIEF DESCRIPTION OF THE DRAWINGS

The invention will be better understood with reference to the detailed description when considered in conjunction with the non-limiting examples and the accompanying drawings, in which:

FIG. 2 provides an illustration of a method of manufacturing an optical sensing device based on surface plasmon resonance (SPR) according to various embodiments.

FIG. 3 provides an illustration of an optical sensing method based on surface plasmon resonance (SPR) according to various embodiments.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Embodiments described in the context of one of the methods or optical sensing devices are analogously valid for the other methods or optical sensing devices. Similarly, embodiments described in the context of a method are analogously valid for an optical sensing device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

The word "over" used with regards to a deposited material formed "over" a side or surface, may be used herein to mean that the deposited material may be formed "directly on", e.g. in direct contact with, the implied side or surface. The word "over" used with regards to a deposited material formed "over" a side or surface, may also be used herein to mean that the deposited material may be formed "indirectly on" the implied side or surface with one or more additional layers being arranged between the implied side or surface and the deposited material. In other words, a first layer "over" a second layer may refer to the first layer directly on the second layer, or that the first layer and the second layer are separated by one or more intervening layers.

The optical sensing device as described herein may be operable in various orientations, and thus it should be understood that the terms "top", "bottom", etc., when used in the following description are used for convenience and to aid understanding of relative positions or directions, and not intended to limit the orientation of the optical sensing device.

In the context of various embodiments, the articles "a", "an" and "the" as used with regard to a feature or element include a reference to one or more of the features or elements.

In the context of various embodiments, the term "about" or "approximately" as applied to a numeric value encompasses the exact value and a reasonable variance.

As used herein, the term "and/or" includes any and all combinations of one or more of the associated listed items.

Figure 1:
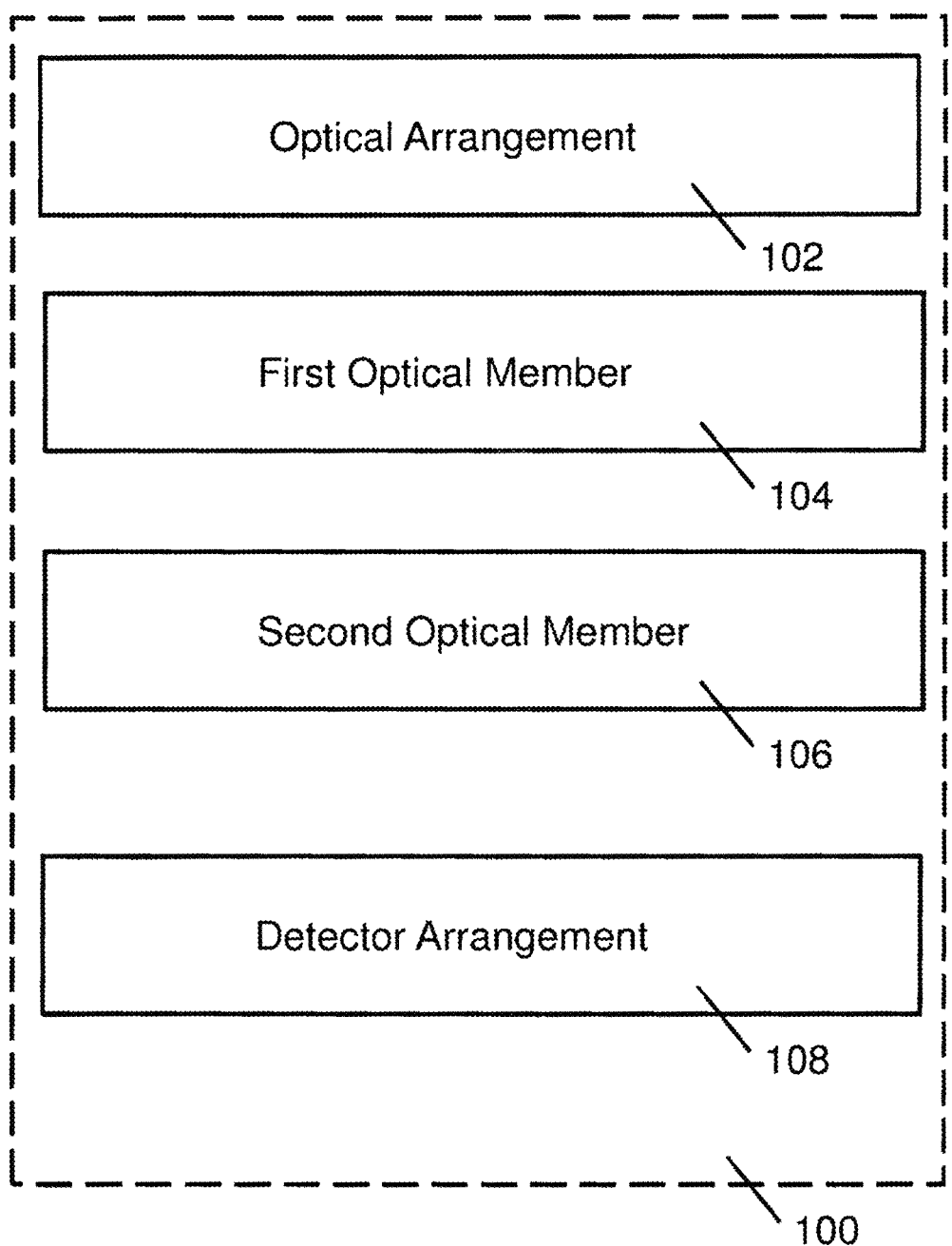
FIG. 1 provides an illustration of an optical sensing device based on surface plasmon resonance (SPR) according to various embodiments.

FIG. 1 provides an illustration of an optical sensing device 100 based on surface plasmon resonance (SPR) according to various embodiments. The optical sensing device 100 may include an optical arrangement 102 configured to provide a first polarization light beam and a second polarization light beam. The optical sensing device 100 may also include a first optical member 104 including a sensing surface, the first optical member 104 configured to receive the first and second polarization light beams and reflect the first and second polarization light beams at the sensing surface. The optical sensing device 100 may further include a second optical member 106 arranged to receive the reflected first and second polarization light beams from the first optical member 104 and configured to separate the reflected first and second polarization light beams in a first direction and a second direction, respectively. The optical device 100 may additionally include a detector arrangement 108 configured to detect the reflected first and second polarization light beams from the second optical member 106.

In other words, the optical sensing device 100 may include an optical arrangement 102 configured to provide beams with different polarizations. The polarized beams may be incident onto the sensing surface of a first optical member. A sample may be on the sensing surface, and the sensing surface may reflect different polarized beams differently due to the sample. The optical sensing device 100 may further include a second optical member 106 which separates the reflected polarized light in different directions, as well as a detector arrangement 108 configured to detect the reflected polarized light.

In various embodiments, the first polarized light beam may have a polarization that is orthogonal to a polarization of the second polarized light beam.

In various embodiments, the first polarization light beam may be a p-polarization light beam and the second polarization may be an s-polarization light beam.

The optical arrangement 102 may include a light source configured for emitting a light beam comprising a first polarization component and a second polarization component, and a third optical member arranged to receive the light beam from the light source and configured to separate the light beam into the first polarization light beam and the second polarization light beam. The third optical member may be a beam splitter.

The first polarization light beam may have the first polarization component, and the second polarization light beam may have the second polarization component. In various embodiments, the first polarization component may be p-polarization, and the second polarization component may be s-polarization.

The light source may be configured to be at a predetermined orientation for emitting the light beam including the first polarization component and the second polarization component. The light beam may have a predetermined wavelength or range of wavelengths. The first polarization light beam and the second polarization light beam may also be at the predetermined wavelength range of wavelengths.

In various embodiments, the light source may be a laser, such as a helium-neon (HeNe) laser. For example, with a HeNe laser, the intensity ratio between p- and s-polarization can be selected/configured by laser orientation.

The predetermined orientation may be about 1° to about 45° from an orientation of the light source which produces a light beam without the second polarization component. The light source may be rotated or oriented at angle selected from a range of 1° to about 45° from a reference orientation in which the light source emits only the first polarization.

In other words, the predetermined orientation of the light source may be at an angle from an orientation of the light source which produces a light beam without the second polarization component (i.e., an angle from the orientation for pure p-polarization laser emission). With such an arrangement/setting, the laser beam provides both p- and s-polarization components (at the predetermined orientation). The angle can be set at about 1° to about 45°. When the angle is less than 45°, it may enhance the intensity of the p-polarization light and may suppress the s-polarization intensity, which in turn enhances the signal to noise ratio in SPR detection.

The first optical member 104 may include a prism, and the sensing surface is provided on a base of the prism. The prism may be configured to allow the first polarization light and the second polarization light to pass through. The prism may be transparent to light at the predetermined wavelength or range of wavelengths. The prism may be a glass prism, and the sensing surface may be a metal surface, such as a gold surface.

The first optical member 104 may also include a flow cell, which may be configured to provide the sample to the sensing surface. The flow cell may include an inlet and an outlet. During operation, a fluid carrying the sample may be introduced into the flow cell so that the sample may be provided to the sensing surface. The fluid may then exit the flow cell through the outlet.

The second optical member 106 may be a polarizing beam splitter. The polarizing beam splitter may be used to split/separate the p- and s-polarization in two different optical paths and no polarizer may be required. For example, in other conventional configurations, no polarizing beam splitter is used. The second optical member 106 may be configured to split or separate the reflected first and second polarization light beams in the first direction and the second direction, which may be different directions.

The polarizing beam splitter may be made of or may include two glass prisms. Alternatively, the polarizing beam splitter may be a half-silvered mirror, or a sheet of glass or plastic with a transparently thin coating of metal, such as aluminum.

The detector arrangement 108 may include a first detector arranged to detect the reflected first polarization light beam and a second detector arranged to detect the reflected second polarization light beam. The first detector and the second detector may be charge-coupled devices (CCD), or may be any other suitable detectors, such as photodiodes or phototransistors.

The first polarization light beam may be modifiable by a surface plasmon wave propagating at the sensing surface during surface plasmon resonance (SPR) and may define a sensing signal. The second polarization light beam may at least be substantially unmodifiable by the surface plasmon wave propagating at the sensing surface during surface plasmon resonance (SPR) and may define a reference signal. In various embodiments, the first polarization light beam may be modified or may be affected by the surface plasmon wave to a greater extent or degree compared to the second polarization light beam. In various other embodiments, the second polarization light beam may be modifiable and may define the sensing signal, while the first polarization light may be substantially unmodifiable, or may less modified or less affected by the surface plasmon wave, and may define the reference signal.

The optical sensing device 100 may additionally include a processor, such as a computer, communicatively coupled to the detector arrangement 108, the processor configured to provide a sensing output based on a difference between the reflected first and second polarization light beams. The difference is a difference in an intensity of the (reflected) first polarization light beam and an intensity of the second (reflected) polarization light beam. The intensity of the (reflected) first polarization light beam may be detected by the first detector and the intensity of the second (reflected) polarization light beam may be detected by the second detector.

The processor may be communicatively coupled to the detector arrangement 108 via an analog-to-digital converter, such as a frame-grabber converter. The analog-to-digital converter or the frame-grabber converter may have one or more inputs coupled to the detector arrangement 108, and one or more outputs coupled to the processor.

The analog-to-digital converter or frame-grabber converter may be configured to convert an analog signal to digital signal for computer processing. The analog-to-digital converter or frame-grabber converter may be configured to receive a first analog signal from a first detector, and may be configured to convert the first analog signal to a first digital signal. The analog-to-digital converter or frame-grabber converter may be further configured to receive a second analog signal from a second detector, and may be configured to convert the second analog signal to a second digital signal. The processor may be configured to receive the first digital signal and the second digital signal.

The processor may be configured to provide a sensing output based on a difference between the reflected first and second polarization light beams. For example, the sensing output may be obtained by the subtraction or difference between the reflected first and second polarization light beams (i.e., p- and s-polarization light beams). From the polarization based subtraction method, experimental results may show that the sensor resolution has been improved to about $10^{-7}$ RIU. The sensing output may be based on the first digital signal and the second digital signal.

In various embodiments, the sensing surface may include a receptor such as an antigen protein, a surface probe deoxyribonucleic acid (DNA), or a protein (e.g. a human serum albumin (HSA protein). The receptor may be immobilized or attached to the sensing surface. The sample may include a molecule such as an antibody, a DNA, or a drug, which may be bound to the receptor upon the sample provided to the sensing surface. The binding of the sample with the receptor may change or generate a surface plasmon propagating at the sensing surface, which may generate or change the sensing signal and/or the reference signal. For instance, when the sample binds with a receptor, a surface plasmon propagating at the sensing surface may be changed, and the sensing signal may be increased, thus increasing the sensing output.

In various embodiments, there may be no requirement for multiple flow cell chambers. In various embodiments, the first optical member 104 may include a single flow cell. For example, the differential intensity measurement between the p- and s-polarization light can be performed between the p- and s-polarization light of the same sensing surface. This may advantageously provide improved signal to noise ratio in SPR detection. For example, in other conventional configurations, the differential approach is between 1) signal from the sample chamber and 2) signal from the water reference chamber. This may be undesirable since two flow cell chambers are required to work together for SPR detection.

FIG. 2 provides an illustration of a method of manufacturing an optical sensing device based on surface plasmon resonance (SPR) according to various embodiments. The method may include, in 202, providing an optical arrangement configured to provide a first polarization light beam and a second polarization light beam. The method may also include, in 204, providing a first optical member including a sensing surface, the first optical member configured to receive the first and second polarization light beams and reflect the first and second polarization light beams at the sensing surface. The method may further include, in 206, providing a second optical member arranged to receive the reflected first and second polarization light beams from the first optical member and configured to separate the reflected first and second polarization light beam in a first direction and a second direction, respectively. The method may also include, in 208, providing a detector arrangement configured to detect the reflected first and second polarization light beams from the second optical member.

In other words, the method may include arranging the optical arrangement, the first optical member, the second optical member, and the detector arrangement in such a way so that the first optical member receives the first and second polarization light beams from the optical arrangement, reflects the first and second polarization light beams at the sensing surface to the second optical member, the second optical member receives the reflected first and second polarization light beams, and separates the reflected first and second polarization light beams in two directions, and the detector arrangement detects the reflected first and second polarization light beams traveling along the two directions.

For avoidance of doubt, it should be noted that the method steps shown in FIG. 2 may not necessarily be in sequence. For instance, the first optical member may be provided before providing the optical arrangement, i.e. step 204 may be before step 202.

The first polarization light beam may be a p-polarization light beam and the second polarization may be an s-polarization light beam.

The optical arrangement may include a light source configured for emitting a light beam comprising a first polarization component and a second polarization component, and a third optical member arranged to receive the light beam from the light source and configured to separate the light beam into the first polarization light beam and the second polarization light beam.

The light source may be configured to be at a predetermined orientation for emitting the light beam including the first polarization component and the second polarization component.

The predetermined orientation may be about 1° to about 45° from an orientation of the light source which produces a light beam without the second polarization component.

The first optical member may include a prism, and the sensing surface may be provided on a base of the prism.

The detector arrangement may include a first detector arranged to detect the reflected first polarization light beam and a second detector arranged to detect the reflected second polarization light beam.

The first polarization light beam may be modifiable by a surface plasmon wave propagating at the sensing surface during SPR and defines a sensing signal, and wherein the second polarization light beam may be at least substantially unmodifiable by the surface plasmon wave propagating at the sensing surface during SPR and may define a reference signal.

The method may further include a processor communicatively coupled to the detector arrangement, the processor configured to provide a sensing output based on a difference between an intensity of the reflected first and second polarization light beams.

FIG. 3 provides an illustration of an optical sensing method based on surface plasmon resonance (SPR) according to various embodiments. The method may include, in 302, providing a sample on a first optical member, the first optical member including a sensing surface on which the sample is provided. The method may also include, in 304, providing, by an optical arrangement, a first polarization light beam and a second polarization light beam to the first optical member. The method may further include, in 306, reflecting the first and second polarization light beams at the sensing surface to provide a reflected first polarization light beam and a reflected second polarization light beam. The method may additionally include, in 308, separating, by a second optical member, the reflecting first and second polarization light beams received from the first optical member in a first direction and a second direction, respectively. The method may also include, in 310, detecting, by a detector arrangement, the reflected first and second polarization light beams from the second optical member.

In other words, the method may include supplying or directing a sample to a sensing surface of the first optical member, and providing a first polarization light beam and a second polarization light beam to the first optical member so that the first polarization light beam and second polarization light beam are reflected at the sensing surface. The reflected first polarization light beam and the reflected second polarization light beam are directed in different directions by the second optical member, and detected by the detector arrangement.

The method may also include providing a receptor on the optical member, e.g. to the sensing surface. The receptor may be provided before providing the sample.

The receptor may be a biological entity or molecule such as an antigen protein, a surface probe deoxyribonucleic acid (DNA), or a protein (e.g. a human serum albumin (HSA protein). The receptor may be immobilized or attached to the sensing surface.

The sample may include a biological entity or molecule such as an antibody, a DNA, or a drug. The sample may be bound to the receptor upon the sample provided to the sensing surface. The binding of the sample with the receptor may change or generate a surface plasmon propagating at the sensing surface, which may generate or change the sensing signal and/or the reference signal. For instance, when the sample binds with a receptor, a surface plasmon propagating at the sensing surface may be changed, and the sensing signal may be increased, thus increasing the sensing output.

The first polarization light beam and the second polarization light beam to the first optical member may be provided to the first optical member after the sample is provided to the first optical member.

The first polarization light beam may be modifiable by a surface plasmon wave propagating at the sensing surface during surface plasmon resonance (SPR) and may define a sensing signal. The second polarization light beam may at least be substantially unmodifiable by the surface plasmon wave propagating at the sensing surface during surface plasmon resonance (SPR) and may define a reference signal. The surface plasmon wave may be generated due to the sample provided to the optical member. The surface plasmon wave may be generated due to the sample bound to the sensing surface of the first optical member.

The method may also include providing a sensing output based on a difference between the reflected first and second polarization light beams.

The method may also include detecting or identifying the sample based on the sensing output, or based on the reflected first and second polarization light beams.

Figure 4:
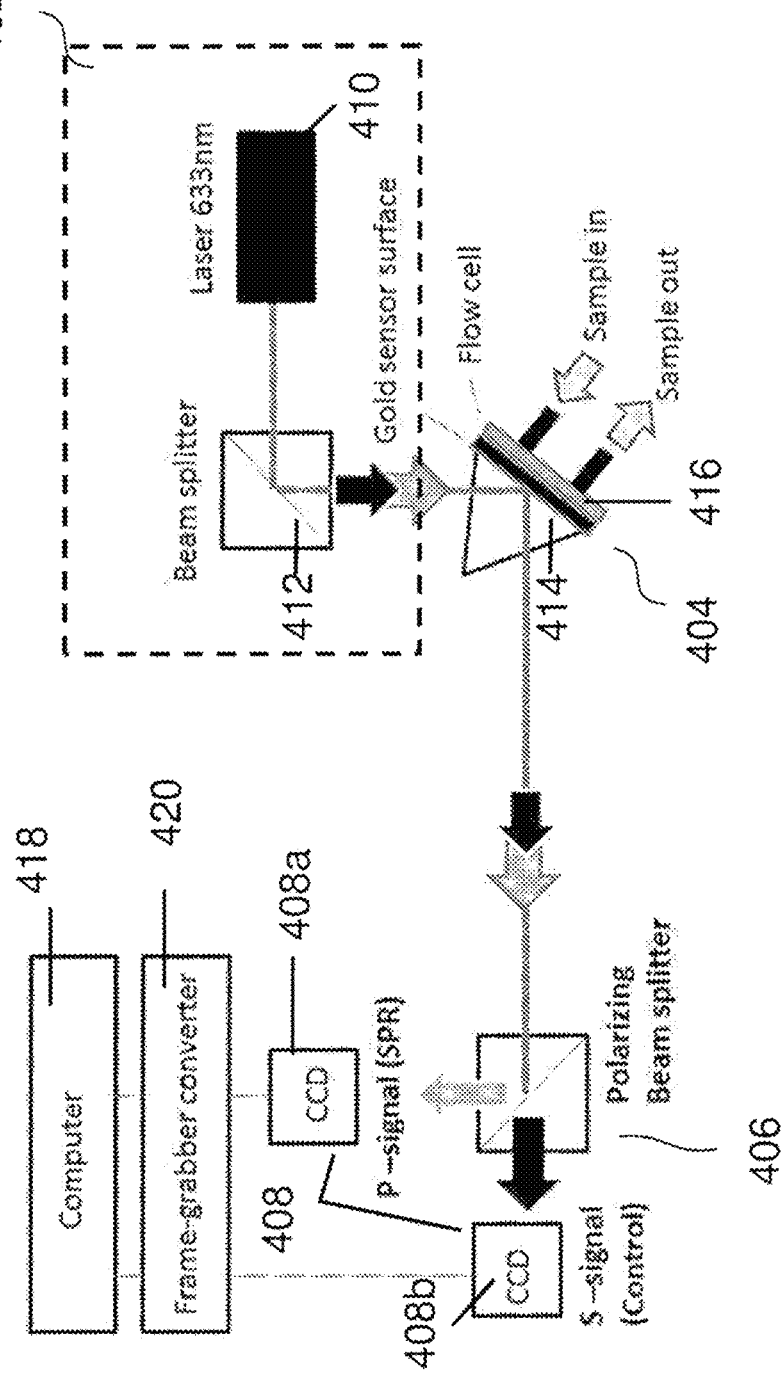
FIG. 4 shows a schematic of an optical sensing device according to various embodiments.

FIG. 4 shows a schematic of an optical sensing device 400 according to various embodiments. The optical sensing device 400 (which may alternatively be referred to as an optical configuration, a surface plasmon resonance (SPR) sensor system, a biosensor, or a plasmonic contrast sensor) may include an optical arrangement 402 configured to provide a first polarization light beam, e.g. a p-polarization light beam, and a second polarization light beam, e.g. a s-polarization light beam. The optical arrangement 402 may include a laser device 410, such as a HeNe laser source, and a beam splitter 412. The orientation of the He—Ne laser source 410 may be set to be 45°, which provides both p- and s-polarization laser light in single laser beam. The laser beam may not be expanded during the detection process, which enhances the intensity contrast during measurement.

The optical sensing device 400 may also include a first optical member 414 including a sensing surface, the first optical member configured to receive the first and second polarization light beams and reflect the first and second polarization light beams at the sensing surface. The first optical member 404 may include a prism 414, and the sensing surface is provided on a base of the prism 414. The first optical member 404 may further include a flow cell 416. The flow cell 416 may include an inlet and an outlet. Fluid carrying a sample may flow through the inlet into the flow cell 416 to provide or supply the sample to the sensing surface, and fluid may flow out of the flow cell 416 through the outlet. The sensing surface may include a suitable material such as gold. Light of both polarizations may be incident on the gold sensing surface of the glass prism 414 and be reflected by the gold sensing surface. At plasmonic resonance, the surface plasmon wave (propagating at the gold sensing surface) may change the p-polarization light beam, while s-polarization light beam may not be affected (due to the wave propagation direction mismatch). The differential measurement of the p-polarization portion and the s-polarization portion may therefore cancel out both optical and electronics noise during measurement, and may thus improve sensor stability and sensor resolution.

The optical sensing device 400 may further include a second optical member 406, such as a polarizing beam splitter, arranged to receive the reflected first and second polarization light beams from the first optical member 404 and configured to separate the reflected first and second polarization light beams, i.e. p-polarization and s-polarization light beams, in a first direction and a second direction, respectively.

The optical device 400 may additionally include a detector arrangement 408 configured to detect the reflected first and second polarization light beams from the second optical member. The detector arrangement 408 may include a first charged-coupled device (CCD) 408a to detect the reflected first polarization light beam, i.e. the p-polarization light, and a second charged-coupled device (CCD) 408b to detect the reflected second polarization light beam, i.e. the s-polarization light. The first charged-coupled device (CCD) 408a may be used to detect a sensing signal (also referred to as response signal) defined by the reflected first polarization light beam, and the second charged-coupled device (CCD) 408b nay be used to detect a reference signal (also referred to as control signal) defined by the reflected second polarization light beam. The sensing and reference signals may be processed with a computer 418 using a suitable software, e.g. Mathlab software.

The sensing and reference signals may first be transmitted to a frame-grabber converter 420, which is coupled to the first charged-coupled device (CCD) 408a and the second charged-coupled device (CCD) 408b. The frame-grabber converter 420 may convert the analog signals into digital signals. The converted digital sensing and reference signals may then be transmitted to the computer 418, which is coupled to the frame-grabber converter 420.

To characterize the response of the intensity SPR sensor, measurements on different concentrations of salt solutions have been performed. The concentrations of salt solution range from 0% to 5%, which correspond to refractive index values from 1.3330 to 1.3418 RIU (refractive index unit). Salt solutions of varying concentrations were injected to the sensing surface for sensor resolution estimation.

Figure 5:
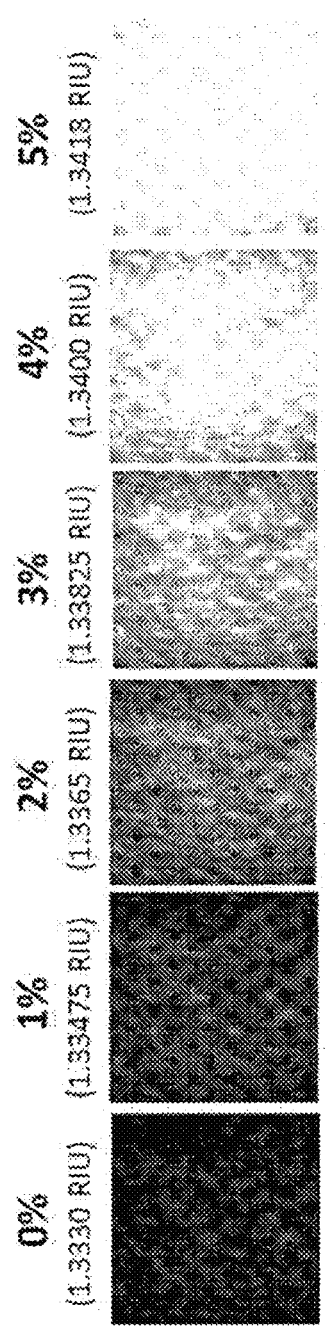
FIG. 5 show images from the sensing signal and reference signal with varying concentrations of salt solution introduced to the sensing surface according to various embodiments.

FIG. 5 show images from the sensing signal and reference signal with varying concentrations of salt solution introduced to the sensing surface according to various embodiments. Images captured from the two CCD cameras 408a, 408b show that the intensity of the response signal increases with increasing salt solution concentration whereas the intensity of the control signal shows no significant change with increasing salt solution concentration. Intensity variations are extracted and the sensor response curve can be plotted.

In FIG. 5, the s-polarization signals (reference/control signal) may appear black because no signal intensity increase has been recorded during SPR detection.

Figure 6:
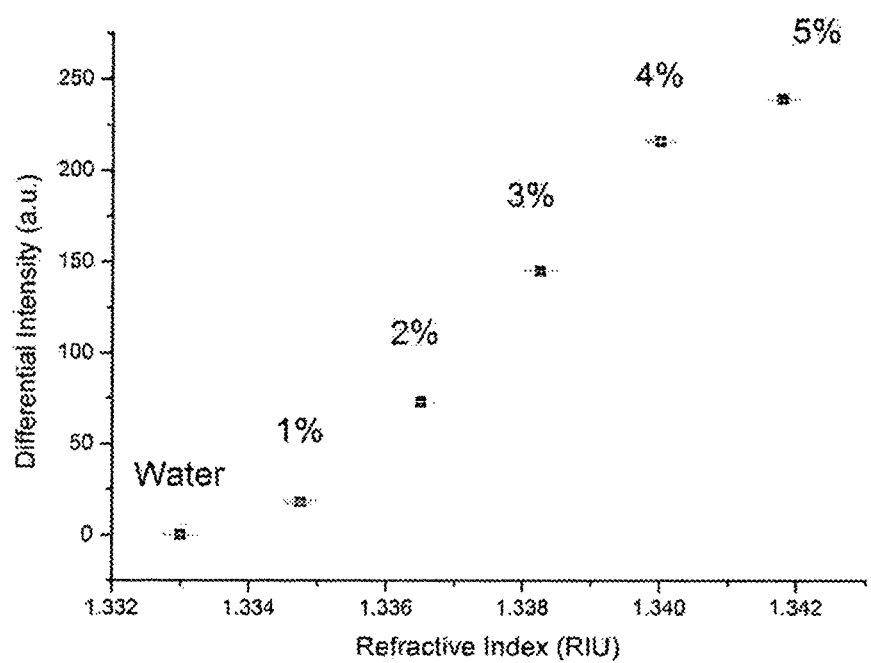
FIG. 6 is a plot of differential intensity (in arbitrary units or a.u.) as a function of refractive index (in refractive index units or RIU) showing the variation of the surface plasmon resonance (SPR) response curve of the device according to various embodiments with salt solution concentrations varying from about 0% to about 5%.

FIG. 6 is a plot 600 of differential intensity (in arbitrary units or a.u.) as a function of refractive index (in refractive index units or RIU) showing the variation of the surface plasmon resonance (SPR) response curve of the device according to various embodiments with salt solution concentrations varying from about 0% to about 5%. The curve in FIG. 6 may be obtained by plotting the average sensor responses at each salt concentration against the refractive index of the salt solution injected. The sensor sensitivity can be obtained from the slope of the sensor response curve according to equation (1).

$$\text{Sensor sensitivity} = (\text{Refractive index changes})/(\text{Sensor Response}) \quad (1)$$

$$\text{Sensor sensitivity} = (1.3400 - 1.33475)/(225.08 - 27.41) = 2.66 \times 10^{-5} \text{ RIU/intensity unit}$$

As shown above, the sensor sensitivity was found to be $2.66 \times 10^{-5}$ RIU/intensity unit (at the linear range 1.33475–1.3400 RIU).

Figure 7:
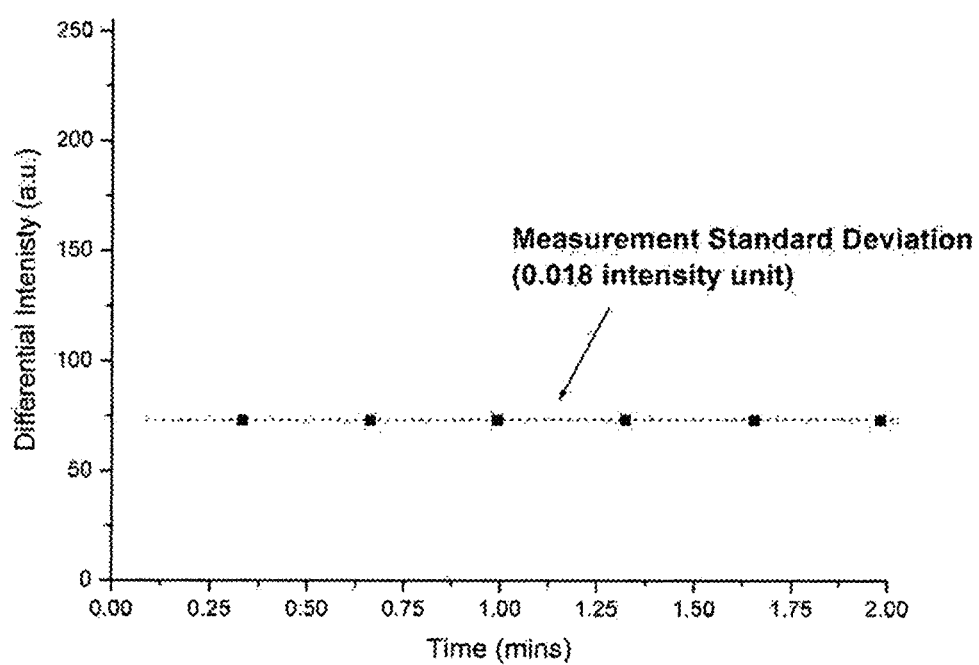
FIG. 7 is a plot of differential intensity (in arbitrary units or a.u.) as a function of time (in minutes or mins) showing characterization of the measurement stability of the device according to various embodiments with about 2% salt solution injection.

FIG. 7 is a plot 700 of differential intensity (in arbitrary units or a.u.) as a function of time (in minutes or mins) showing characterization of the measurement stability of the device according to various embodiments with about 2% salt solution injection. The characterization may be obtained using the measurement standard deviation (S.D.) value of 0.018 intensity unit over 5 averaged data points. The sensor resolution can further be obtained from the slope of the sensor response curve according to equation (2).

$$\text{Sensor resolution} = \text{Sensitivy} \times \text{Measurement Stability} \quad (2)$$

$$\text{Sensor resolution} = (2.66 \times 10^{-5}) \times (0.018)$$

$$= 4.79 \times 10^{-7} RIU$$

In order to calculate the sensor resolution of the system, water sample was injected into the flow chamber at the prism. The measurement standard deviation obtained was 0.018 intensity response. According to equation (2), the sensor resolution was found to be $4.79 \times 10^{-7}$ RIU, which is better than reported conventional intensity SPR sensor at $10^{-5}$ RIU by two orders of magnitude.

The sensor has further been demonstrated for the detections of different biomolecular hinging interactions, including antigen-antibody, DNA-DNA, protein-small molecule/drug molecular bindings.

Antibody-Antigen Binding

H3N2 antigen protein was immobilized on the gold sensor surface of the sensor. During detection, the sensor surface was first kept under PBS buffer solution. Then, H3N2 antibody (40 ug/ml) was injected and the specific antigens-antibodies bindings were measured in real-time.

Figure 8A:
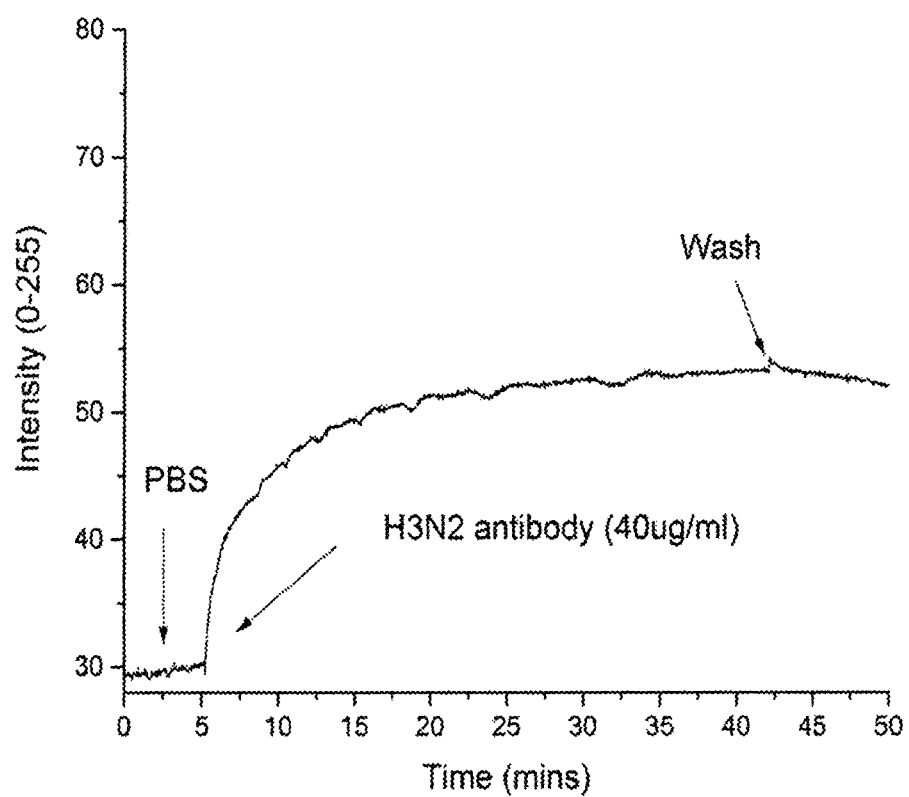
FIG. 8A is a plot of intensity (in arbitrary units from 0 to 255) as a function of time (in minutes or mins) showing experimental results on H3N2 antigen-antibody binding detection according to various embodiments.

FIG. 8A is a plot 800a of intensity (in arbitrary units from 0 to 255) as a function of time (in minutes or mins) showing experimental results on H3N2 antigen-antibody binding detection according to various embodiments.

Deoxyribonucleic Acid (DNA)—Deoxyribonucleic Acid (DNA) Binding

In the second experiment, surface probe DNA was immobilized on gold sensor surface. At 18 mins of the experiment, DNA sample (extracted from E-coli bacteria, 100 uM) was injected and the specific DNA-DNA bindings were recorded and the measurement results.

Figure 8B:
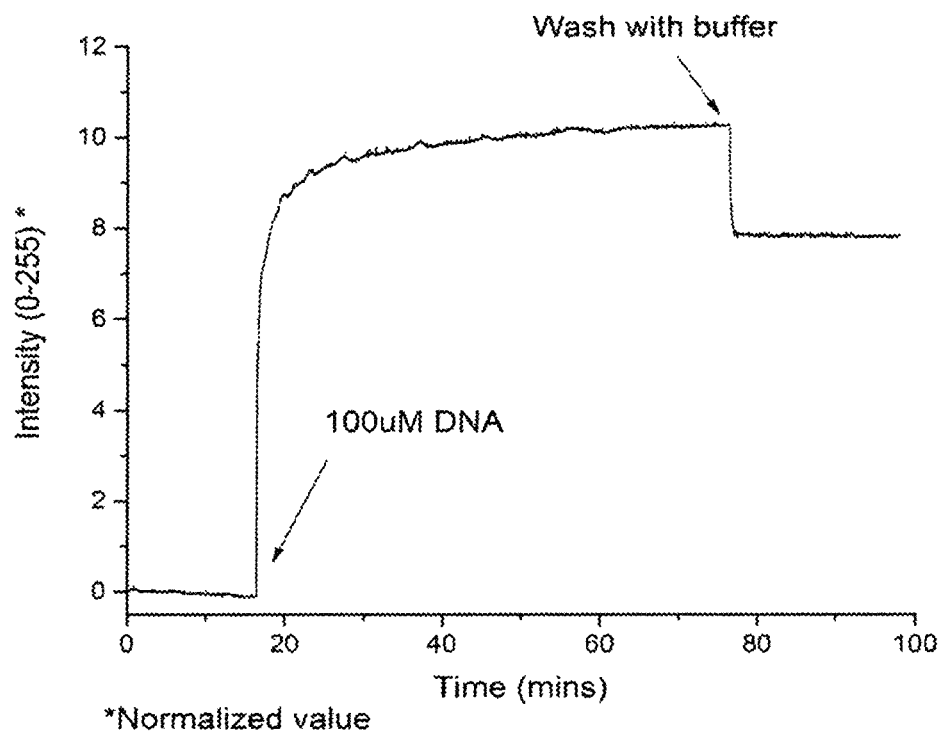
FIG. 8B is a plot of intensity (in arbitrary units from 0 to 255) as a function of time (in minutes or mins) showing experimental results on deoxyribonucleic acid (DNA)—deoxyribonucleic acid (DNA) binding detection according to various embodiments.

FIG. 8B is a plot 800b of intensity (in arbitrary units from 0 to 255) as a function of time (in minutes or mins) showing experimental results on deoxyribonucleic acid (DNA)—deoxyribonucleic acid (DNA) binding detection according to various embodiments.

Protein—Drug Binding

Furthermore, human serum albumin (HAS) protein was immobilized on gold sensor surface. During detection, the small molecule, Warfarin (<500 Da, 2 mM), was injected and the protein-small molecule bindings were measured.

Figure 8C:
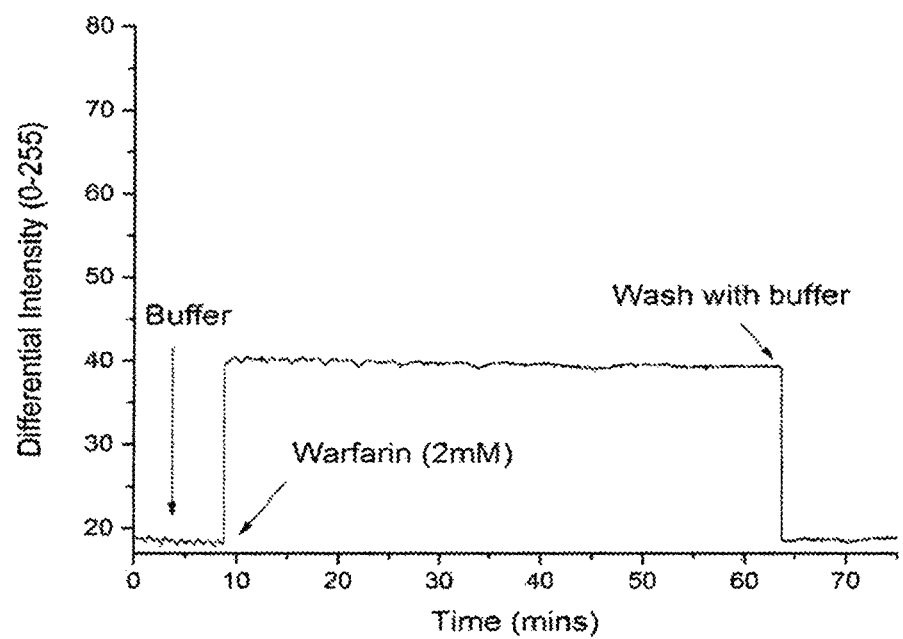
FIG. 8C is a plot of intensity (in arbitrary units from 0 to 255) as a function of time (in minutes or mins) showing experimental results on human serum albumin (HAS) protein—Warfarin binding detection according to various embodiments.

FIG. 8C is a plot 800c of intensity (in arbitrary units from 0 to 255) as a function of time (in minutes or mins) showing experimental results on human serum albumin (HAS) protein—Warfarin binding detection according to various embodiments.

It may be envisioned that the device may be used for detection of other substances or biomolecules. It may also be envisioned that the device may be used in conjunction with other receptors.

Various embodiments a biosensor based on differential plasmonic contrast. In various embodiments, the orientation of the He—Ne laser source may be set to be 45°, which provides both p- and s-polarization laser light in single laser beam. At plasmonic resonance, the surface plasmon wave (propagating at the gold sensing surface) may change the p-polarization light, while s-polarization may not be affected (due to the wave propagation direction mismatch). The differential measurement between p- and s-polarization portion may therefore cancel out both optical and electronics noise during measurement and improve the sensor stability and sensor resolution.

In addition, two separated CCDs may be used for the detection of p- and s-polarization, which enlarge the imaging pixels used for signal processing and provide further improvements in sensor resolution.

The laser beam may not be expanded during the detection process. It may enhance the intensity contrast and may produce enhanced sensor sensitivity.

No polarizer may be required in the device according to various embodiments.

With all the configurations and features mentioned above, the performance of the differential plasmonic contrast sensor according to various embodiments may be found to be ($10^{-7}$ RIU), which may be two orders of magnitude better than that of the conventional intensity based SPR sensor at ($10^{-5}$ RIU).

Various embodiments may be one order of magnitude better than conventional setups.

Various embodiments may be used for different biomolecular interactions detection, including 1) antigen-antibody binding, 2) DNA-RNA binding, and 3) protein-drug binding.

Various embodiment may employ binding detection, and may applications in analytical detection or drug discovery.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. An optical sensing device based on surface plasmon resonance (SPR), the optical sensing device comprising:
  an optical arrangement configured to provide a p-polarization light beam and a s-polarization light beam;
  a prism comprising a sensing surface at a base of the prism, the prism configured to receive the p-polarization light beam and the s-polarization light beam and reflect the p-polarization light beam and the s-polarization light beam at the sensing surface;
  a polarizing beam splitter arranged to receive the reflected p-polarization light beam and the reflected s-polarization light beam from the prism and configured to separate the reflected p-polarization light beam and the reflected s-polarization light beam in a first direction and a second direction, respectively; and
  a detector arrangement configured to detect the reflected p-polarization light beam and the reflected s-polarization light beam from the polarizing beam splitter;
  wherein the optical arrangement comprises:
    a light source configured for emitting a light beam comprising a p-polarization component and a s-polarization component; and an initial beam splitter arranged between the light source and the prism, the initial beam splitter configured to receive the light beam from the light source and configured to separate the light beam into the p-polarization light beam and the s-polarization light beam;

wherein the light source is configured to be at a predetermined orientation for emitting the light beam comprising the p-polarization component and the s-polarization component, the predetermined orientation being 1° to less than 45° from an orientation of the light source which produces a light beam without the s-polarization component.

2. The optical sensing device according to claim 1, wherein the detector arrangement comprises a first detector arranged to detect the reflected p-polarization light beam and a second detector arranged to detect the reflected s-polarization light beam.

3. The optical sensing device according to claim 1, wherein the p-polarization light beam is modifiable by a surface plasmon wave propagating at the sensing surface during SPR and defines a sensing signal, and wherein the s-polarization light beam is at least substantially unmodifiable by the surface plasmon wave propagating at the sensing surface during SPR and defines a reference signal.

4. The optical sensing device according to claim 1, further comprising:
a processor communicatively coupled to the detector arrangement, the processor configured to provide a sensing output based on a difference between the reflected p-polarization light beam and the reflected s-polarization light beam.

5. The optical sensing device according to claim 4, wherein the difference is a difference in an intensity of the p-polarization light beam and an intensity of the s-polarization light beam.

6. A method of manufacturing an optical sensing device based on surface plasmon resonance (SPR), the method comprising:
providing an optical arrangement configured to provide a p-polarization light beam and a s-polarization light beam;
providing a prism comprising a sensing surface at a base of the prism, the prism configured to receive the p-polarization light beam and the s-polarization light beam and reflect the p-polarization light beam and the s-polarization light beam at the sensing surface;
providing a polarizing beam splitter arranged to receive the reflected p-polarization light beam and the reflected s-polarization light beam from the prism and configured to separate the reflected p-polarization light beam and the reflected s-polarization light beam in a first direction and a second direction, respectively; and
providing a detector arrangement configured to detect the reflected p-polarization light beam and the reflected s-polarization light beam from the polarizing beam splitter;
wherein the optical arrangement comprises:
a light source configured for emitting a light beam comprising a p-polarization component and a s-polarization component; and
an initial beam splitter arranged between the light source and the prism, the initial beam splitter configured to receive the light beam from the light source and configured to separate the light beam into the p-polarization light beam and the s-polarization light beam;

wherein the light source is configured to be at a predetermined orientation for emitting the light beam comprising the p-polarization component and the s-polarization component, the predetermined orientation being 1° to less than 45° from an orientation of the light source which produces a light beam without the s-polarization component.

7. The method according to claim 6, wherein the detector arrangement comprises a first detector arranged to detect the reflected p-polarization light beam and a second detector arranged to detect the reflected s-polarization light beam.

8. The method according to claim 6, wherein the p-polarization light beam is modifiable by a surface plasmon wave propagating at the sensing surface during surface plasmon resonance (SPR) and defines a sensing signal, and wherein the s-polarization light beam is at least substantially unmodifiable by the surface plasmon wave propagating at the sensing surface during surface plasmon resonance (SPR) and defines a reference signal.

9. The method according to claim 6, further comprising:
a processor communicatively coupled to the detector arrangement, the processor configured to provide a sensing output based on a difference between an intensity of the reflected p-polarization light beam and the reflected s-polarization light beam.

10. An optical sensing method based on surface plasmon resonance (SPR), the method comprising:
providing a sample on a prism, the prism comprising a sensing surface on which the sample is provided, the sensing surface at a base of the prism;
providing, by an optical arrangement, a p-polarization light beam and a s-polarization light beam to the prism;
reflecting the p-polarization light beam and s-polarization light beam at the sensing surface to provide a reflected p-polarization light beam and a reflected s-polarization light beam;
separating, by a polarizing beam splitter, the reflected p-polarization light beam and the reflected s-polarization light beam received from the prism in a first direction and a second direction, respectively; and
detecting, by a detector arrangement, the reflected p-polarization light beam and the reflected s-polarization light beam from the polarizing beam splitter;
wherein the optical arrangement comprises:
a light source configured for emitting a light beam comprising a p-polarization component and a s-polarization component; and
an initial beam splitter arranged between the light source and the prism, the initial beam splitter configured to receive the light beam from the light source and configured to separate the light beam into the p-polarization light beam and the s-polarization light beam;

wherein the light source is configured to be at a predetermined orientation for emitting the light beam comprising the p-polarization component and the s-polarization component, the predetermined orientation being 1° to less than 45° from an orientation of the light source which produces a light beam without the s-polarization component.

* * * * *